United States Patent [19]

Musleve et al.

[11] Patent Number: 5,663,396

[45] Date of Patent: Sep. 2, 1997

[54] PREPARATION OF SULFUR-CONTAINING ORGANOSILICON COMPOUNDS

[75] Inventors: Richard Thomas Musleve, Akron; Dane Kenton Parker, Massillon; Robert Charles Hirst, Akron, all of Ohio

[73] Assignee: The Goodyear Tire & Rubber Company, Akron, Ohio

[21] Appl. No.: 740,570

[22] Filed: Oct. 31, 1996

[51] Int. Cl.$^6$ ...................................................... C07F 7/08
[52] U.S. Cl. ............................................................ 556/427
[58] Field of Search .............................................. 556/427

[56] References Cited

U.S. PATENT DOCUMENTS

| | | | |
|---|---|---|---|
| 3,842,111 | 10/1974 | Meyer-Simon et al. | 260/448.2 E |
| 3,873,489 | 3/1975 | Thurn et al. | 260/33.6 AQ |
| 3,978,103 | 8/1976 | Meyer-Simon et al. | 260/448.8 R |
| 3,997,581 | 12/1976 | Pietka et al. | 260/448.8 R |
| 4,129,585 | 12/1978 | Buder et al. | 260/448.8 R |
| 4,384,132 | 5/1983 | Schwarz et al. | 556/427 |
| 4,401,598 | 8/1983 | Karl et al. | 260/349 |
| 4,408,064 | 10/1983 | Schwarz et al. | 556/427 |
| 4,433,164 | 2/1984 | Jenck | 560/207 |
| 4,507,490 | 3/1985 | Panster et al. | 556/427 |
| 4,595,740 | 6/1986 | Panster | 556/427 X |
| 4,946,977 | 8/1990 | Bernhardt et al. | 556/440 |
| 5,110,969 | 5/1992 | Dittrich et al. | 556/427 |
| 5,405,985 | 4/1995 | Parker et al. | 556/427 |
| 5,468,893 | 11/1995 | Parker et al. | 556/427 |
| 5,489,701 | 2/1996 | Childress et al. | 556/427 |
| 5,583,245 | 12/1996 | Parker et al. | 556/427 |
| 5,596,116 | 1/1997 | Childress et al. | 556/427 |

FOREIGN PATENT DOCUMENTS

| | | |
|---|---|---|
| 0024926 | 8/1980 | European Pat. Off. . |
| 0029176 | 11/1980 | European Pat. Off. . |
| 0483479 | 8/1991 | European Pat. Off. . |
| 0483480 | 8/1991 | European Pat. Off. . |
| 1484909 | 9/1977 | United Kingdom . |

OTHER PUBLICATIONS

Deng Peng and Chen Jia–Yong's "Disproportionation Reaction of Elemental Sulfur by Phase Transition Catalysis," *Journal of Inorganic Chemistry*, 3(4):128–130 (1987).
S. Wolff, et al., Eur. Rubber J., 16, Jan. 1994.
K. E. Koenig, et al., Tet. Lett., 2275 (1974).
Results from a computerized technical search.

*Primary Examiner*—Paul F. Shaver
*Attorney, Agent, or Firm*—Bruce J. Hendricks

[57] ABSTRACT

The present invention relates to a process for the production of organosilicon compounds of the formula

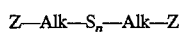

$$Z-Alk-S_n-Alk-Z \qquad (I)$$

in which Z is selected from the group consisting of

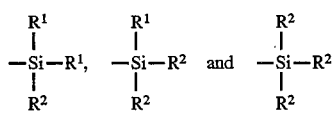

where $R^1$ is an alkyl group of 1 to 4 carbon atoms, cyclohexyl or phenyl;

$R^2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising (A) reacting sodium hydroxide with sulfur in the presence of a saturated NaCl aqueous solution to form a reaction mixture;

(B) reacting said reaction mixture with a compound of the formula:

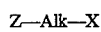

$$Z-Alk-X \qquad (II)$$

where X is Cl or Br; in the presence of a phase transfer catalyst.

17 Claims, No Drawings

PREPARATION OF SULFUR-CONTAINING ORGANOSILICON COMPOUNDS

BACKGROUND

Sulfur containing organosilicon compounds are useful as reactive coupling agents between rubber and silica fillers providing for improved physical properties. They are also useful as adhesion primers for glass, metals and other substrates.

U.S. Pat. Nos. 3,842,111, 3,873,489 and 3,978,103 disclose the preparation of various sulfur containing organosilicon compounds. These organosilicon compounds are prepared by reacting (1) 2 moles of a compound of the formula $$Z\text{—Alk—hal}$$

where hal is a chlorine, bromine or iodine; Z is

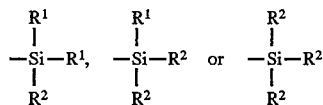

where $R^1$ is an alkyl of 1 to 4 carbon atoms or phenyl and $R^2$ is alkoxy of 1 to 8 carbon atoms, cycloalkoxy of 5 to 8 carbon atoms or alkylmercapto with 1 to 8 carbon atoms; Alk is a divalent aliphatic hydrocarbon or unsaturated hydrocarbon or a cyclic hydrocarbon containing 1 to 18 carbon atoms; with (2) 1 mole of a compound of the formula $$Me_2S_n$$

where Me is ammonium or a metal atom and n is a whole number from 2 to 6. Since the two starting materials are liquid, the reaction can take place in the absence of a solvent; however, a volatile inert organic solvent is not only generally used but is preferred. The reaction is carried out with the exclusion of water. The reason for the exclusion of water is to avoid the alkaline hydrolysis reaction of the silyl alkoxy groups which will ultimately lead to insoluble polymeric by-products and lower the overall yield of desired product. Representative organic solvents include aliphatic alcohols such as methyl alcohol and ethyl alcohol. At the end of the reaction between the two starting materials, the separated salt is removed by filtration. The filtrate is then freed from the solvent by distillation under vacuum. Unfortunately, this process suffers from many practical problems. Many of these problems relate to the solvent, e.g. ethyl alcohol. Ethyl alcohol has a low flash point. In addition, it is difficult to obtain and maintain in the water-free (anhydrous) state.

U.S. Pat. No. 5,405,985 relates to a process for the production of organosilicon compounds of the formula $$Z\text{—Alk—}S_n\text{—Alk—}Z$$

in which Z is selected from the group consisting of

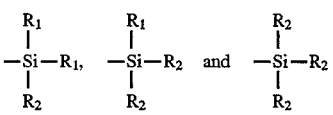

where $R_1$ is an alkyl group of 1 to 4 carbon atoms, cyclohexy or phenyl;
$R_2$ is alkoxy of 1 to 8 carbon atoms or cycloalkoxy of 5 to 8 carbon atoms;
Alk is a divalent hydrocarbon of 1 to 18 carbon atoms and n is an integer of 2 to 8; comprising reacting
(A) a compound of the formula $$Z\text{—Alk—X}$$

where X is Cl, Br or I; with (B) a compound of the formula $$Me_1S_n$$

where Me is ammonium or an alkali metal;
wherein the reaction is conducted in the presence of a phase transfer catalyst and an aqueous phase.

U.S. Pat. No. 5,468,893 relates to a process for the production of organosilicon compounds of the formula $$Z\text{—Alk—}S_n\text{Alk—}Z$$

in which Z is selected from the group consisting of

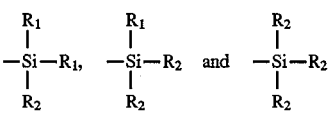

where $R_1$ is an alkyl group of 1 to 4 carbon atoms, cyclohexyl or phenyl;
$R_2$ is alkoxy of 1 to 8 carbon atoms or cycloalkoxy of 5 to 8 carbon atoms;
Alk is a divalent hydrocarbon of 1 to 18 carbon atoms and n is an integer of 2 to 8; comprising reacting
(A) a compound of the formula $$Z\text{—Alk—X}$$

when X is Cl, Br or I; with (B) a compound of the formula $$Me_2S_n$$

where Me is ammonium or an alkali metal;
wherein the reaction is conducted in the presence of a phase transfer catalyst an aqueous phase and a salt of the formula $$XY$$

or $$X_2SO_4$$

where X is selected from the group consisting of Li, Na, K, Rb and Cs; and where Y is selected from the group consisting of F, Cl and Br.

SUMMARY OF THE INVENTION

The present invention relates to a process for the production of sulfur containing organosilicon compounds. The process involves reacting (A) reacting sodium hydroxide with sulfur in the presence of a saturated NaCl aqueous solution to form a reaction mixture; and (B) reacting said reaction mixture with a haloalkylsilane compound in the presence of a phase transfer catalyst.

DETAILED DESCRIPTION OF THE INVENTION

There is disclosed a process for the production of organosilicon compounds of the formula $$Z-Alk-S_n-Alk-Z \qquad (I)$$

in which Z is selected from the group consisting of

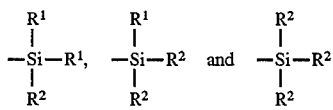

where $R^1$ is an alkyl group of 1 to 4 carbon atoms, cyclohexyl or phenyl;

$R^2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising reacting (A) reacting sodium hydroxide with sulfur in the presence of a saturated NaCl aqueous solution to form a reaction mixture; and (B) reacting said reaction mixture with a compound of the formula:

$$Z-Alk-X \qquad (II)$$

where X is Cl or Br; in the presence of a phase transfer catalyst.

Examples of sulfur containing organosilicon compounds which may be prepared in accordance with the present invention include: 3,3'-bis(trimethoxysilylpropyl) disulfide, 3,3'-bis(triethoxysilylpropyl) tetrasulfide, 3,3'-bis (triethoxysilylpropyl) octasulfide, 3,3'-bis (trimethoxysilylpropyl) tetrasulfide, 2,2'-bis (triethoxysilylethyl) tetrasulfide, 3,3'-bis (trimethoxysilylpropyl) trisulfide, 3,3'-bis (triethoxysilylpropyl) trisulfide, 3,3'-bis (tributoxysilylpropyl) disulfide, 3,3'-hexasulfide, 3,3'-bis (trimethoxysilylpropyl) octasulfide, 3,3'-bis (trimethoxysilylpropyl) tetrasulfide, 3,3'-bis (trioctoxysilylpropyl) bis(trihexoxysilylpropyl) disulfide, 3,3'-bis(tri-2"-ethylhexoxysilylpropyl) trisulfide, 3,3'-bis (triisooctoxysilylpropyl) tetrasulfide, 3,3'-(tri-t-butoxysilylpropyl) disulfide, 2,2'-bis (methoxy diethoxy silyl ethyl) tetrasulfide, 2,2'-bis (tripropoxysilylethyl) pentasulfide, 3,3'-bis (tricyclonexoxysilylpropyl) tetrasulfide, 3,3'-bis (tricyclopentoxysilylpropyl) trisulfide, 2,2'-bis (tri-2"-methylcyclohexoxysilylethyl) tetrasulfide, bis (trimethoxysilylmethyl) tetrasulfide, 3-methoxy ethoxy propoxysilyl 3,'-diethoxybutoxy-silylpropyltetrasulfide, 2,2'-bis(dimethyl methoxysilylethyl) disulfide, 2,2,'-bis (dimethyl sec.butoxysilylethyl) trisulfide, 3,3'-bis(methyl butylethoxysilylpropyl) tetrasulfide, 3,3'-bis(di t-butylmethoxysilylpropyl) tetrasulfide, 2,2'-bis(phenyl methyl methoxysilylethyl) trisulfide, 3,3'-bis(diphenyl isopropoxysilylpropyl) tetrasulfide, 3,3,'-bis(diphenyl cyclohexoxysilylpropyl) disulfide, 3,3'-bis(dimethyl ethylmercaptosilylpropyl) tetrasulfide, 2,2'-bis(methyl dimethoxysilylethyl) trisulfide, 2,2'-bis(methyl ethoxypropoxysilylethyl) tetrasulfide, 3,3,'-bis(diethyl methoxysilylpropyl) tetrasulfide, 3,3'-bis(ethyl di-sec. butoxysilylpropyl) disulfide, 3,3'-bis(propyl diethoxysilylpropyl) disulfide, 3,3'-bis(butyl dimethoxysilylpropyl) trisulfide, 3,3'-bis(phenyl dimethoxysilylpropyl) tetrasulfide, 3-phenyl ethoxybutoxysilyl 3,'-trimethoxysilylpropyl tetrasulfide, 4,4,'-bis (trimethoxysilylbutyl) tetrasulfide, 6,6,'-bis (triethoxysilylhexyl) tetrasulfide, 12,12'-bis (triisopropoxysilyl dodecyl) disulfide, 18,18'-bis (trimethoxysilyloctadecyl) tetrasulfide, 18,18'-bis (tripropoxysilyloctadecenyl) tetrasulfide, 4,4'-bis (trimethoxysilyl-buten-2-yl) tetrasulfide, 4,4'-bis (trimethoxysilylcyclohexylene) tetrasulfide, 5,5'-bis (dimethoxymethylsilylpentyl) trisulfide, 3,3'-bis (trimethoxysilyl-2-methylpropyl) tetrasulfide and 3,3'-bis (dimethoxyphenylsilyl-2-methylpropyl) disulfide.

The preferred sulfur containing organosilicon compounds which are prepared in accordance with the present invention are the 3,3'-bis(trimethoxy or triethoxy silylpropyl) polysulfides. The most preferred compound is 3,3'-bis (triethoxysilylpropyl) disulfide. Therefore as to formula I, preferably Z is

where $R^2$ is an alkoxy of 2 to 4 carbon atoms, with 2 carbon atoms being particularly preferred; Alk is a divalent hydrocarbon of 2 to 4 carbon atoms with 3 carbon atoms being particularly preferred; and n is an integer of from 2 to 6 with 2 being particularly preferred.

In the first step of the process of the present invention, sodium hydroxide is reacted with sulfur in the presence of a saturated NaCl aqueous solution. It is believed that the sulfur may react with the sodium hydroxide to form an intermediate polysulfidic ion which subsequently reacts with the haloalkylsilane.

By varying the molar ratio of the sulfur to sodium hydroxide, one can control the resultant reaction product. Generally speaking, the molar ratio of the sulfur to sodium hydroxide ranges from 4:1 to 1:28. If one desires a higher concentration of a disulfide product (where n is 2), one uses a molar excess of sodium hydroxide, such as a molar ratio of 1:16. If one desires a higher concentration of a tetrasulfide product (where n is 4), one uses a higher concentration of sulfur; for example, 1:1 to 4:1.

As mentioned above, the reaction between the sodium hydroxide and sulfur is conducted in the presence of a saturated NaCl aqueous solution (brine). The volume of brine that is present may vary. The concentration of the two reactants in the brine generally ranges from about 20 to 50 percent by weight. Preferably, the concentration of the sodium hydroxide and sulfur in the brine ranges from about 25 to 45 percent.

The reaction between the sodium hydroxide and sulfur may be conducted at a variety of temperatures. Generally speaking, the reaction is conducted at a temperature ranging from about 75° to 100° C. Preferably, the reaction is conducted at a temperature ranging from about 85° to 95° C.

The reaction between the sodium hydroxide and sulfur is a relatively quick reaction. For example, the complete reaction may range from about 5 to 30 minutes.

Once the reaction between the sodium hydroxide and sulfur is complete and the polysulfidic ions are formed, the reaction mixture is reacted with the halogenated silane of formula II.

With respect to formula II, representative examples include the halogenated (chloro and bromo) substituted forms of ethyl triethoxy silane, propyl triethoxy silane, butyl triethoxy silane, pentyl triethoxy silane, hexyl triethoxy silane, heptyl triethoxy silane, actyl triethoxy silane, nonyl triethoxy silane, decyl triethoxy silane, undecyl triethoxy silane, dodecyl triethoxy silane, tridecyl triethoxy silane, tetradecyl triethoxy silane and pentadecyl triethoxy silane to name a few.

By varying the molar ratio of the compound of formula II to the reaction mixture containing the polysulfidic ion, one can control the resultant reaction product. Generally speaking, the molar ratio of the compound of formula II to polysulfidic ion ranges from 1:1 to greater than 1:5. If one desires a higher concentration of a disulfide product (where n is 2), one uses a molar ratio of 1:3 or greater. If one desires a higher concentration of a tetrasulfide product (where n is 4), one uses a lower molar excess of polysulfidic ion.

The reaction between the compound of formula II and the polysulfidic ion is conducted in the presence of a phase transfer catalyst. Representative phase transfer catalysts may have a quaternary onium cation of the following structural formulae (III), (IV) or (V):

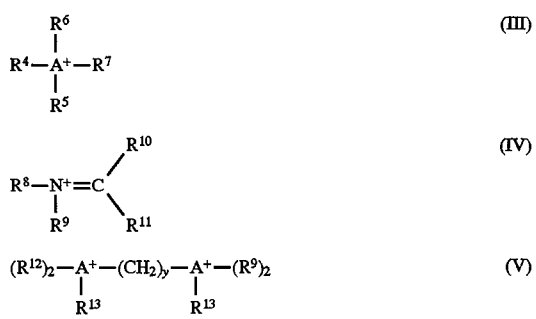

wherein A represents nitrogen, phosphorus or arsenic; $R^4$, $R^5$, $R^6$, $R^7$, which may be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms, preferably from 4 to 8 carbon atoms and most preferably an alkenyl radical derived from the starting material conjugated diene; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms, $R^8$, $R^9$, $R^{10}$, $R^{11}$, which also may be the same or different, are each a linear or branched chain alkyl radical containing from 1 to 4 carbon atoms; with the proviso that the $R^{10}$, and $R^{11}$ radicals may together form an alkylene radical containing from 3 to 6 carbon atoms; and with the further proviso that the $R^9$ and $R^{10}$ or $R^9$ and $R^{11}$ radicals may together form an alkylene, alkenylene or alkadienylene radical containing 4 carbon atoms and, together with the nitrogen atom, comprising a 5-membered nitrogen heterocycle; $R^{12}$ is a linear or branched chain alkyl radical containing from 1 to 4 carbon atoms, or a phenyl radical; $R^{13}$ is a linear or branched chain alkyl radical containing from 1 to 4 carbon atoms, and which may be the same or different from $R^{12}$, a linear or branched chain alkenyl radical containing from 2 to 12 carbon atoms, preferably from 4 to 8 carbon atoms, and more preferably an alkenyl radical derived from the starting material conjugated diene to be carbonylated; and y is an integer of from 1 to 10, and preferably less than or equal to 6.

Exemplary of the quaternary onium cations having the structural Formula III, the following are representative: tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$-$C_{10}$) ammonium, methyltriphenylammonium, buten-2-yltriethylammonium, N,N-dimethyltetramethyleneammonium, N,N-diethyltetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl) phosphonium, methyl-tri(n-propyl)phosphonium, methyl-tri (n-butyl)phosphonium, methyl-tri(2-methylpropyl) phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl) phosphonium, butyltriphenylphosphonium, benzyltriphenylphosphonium, (β-phenylethyl) dimethylphenylphosphonium, tetraphenylphosphonium, triphenyl(4-methylphenyl)phosphonium, tetrakis (hydroxymethyl)phosphonium, tetrakis(2-hydroxyethyl) phosphonium and tetraphenylarsonium.

And exemplary of the Formula V cations are the following: N-methylpyridinium, N-ethylpyridinium, N-hexadecylpyridinium and N-methylpicolinium.

Among the cations having the structural Formula V, the following are representative: 1,2-bis(trimethylammonium) ethane, 1,3-bis(trimethylammonium)propane, 1,4-bis (trimethylammonium)butane and 1,3-bis(trimethylammonium)butane.

Representative of the anions of said onium salts include the following ions: $F^-$, $ClO_4^-$, $PF_6^-$, $BF_4^-$, tetraphenylborate anion, $PO_4^{-3}$, $HPO_4^{-2}$, $H_2PO_4^-$, $CH_3SO_3^-$,

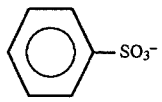

$HSO_4^-$, $NO_3^-$, $SO_4^{-2}$, $Cl^-$, and $Br^-$. Preferably, the anion is $Cl^-$ or $Br^-$.

A particularly preferred onium salt that is used is tetrabutylammonium bromide.

The amount of onium salt that is used in the process of the present invention may vary. Generally speaking, the amount of onium salt will range from about 0.1 to 10 mol percent, relative to the compound of formula II, with a range of from 1 to 5 mole percent being preferred.

Wherein the phase transfer catalyst may be added to the reaction at any time, from a practical standpoint, the catalyst is preferably added to the reaction mixture all at once or portionwise at a temperature between 65°–90° C. as a solid or concentrated (40–50 percent) aqueous solution.

The reaction between the polysulfidic ion and the halogenated silane of formula II is conducted in aqueous solution; however, one may optionally use a two phase aqueous/organic system. In fact, it is preferred to use an aqueous/organic system because the presence of the organic phase assists in the phase separation upon completion of the reaction. When the organic phase is used, preferably the halogenated silane compound of formula II is predissolved in the organic phase prior to addition to the reaction mixture containing the polysulfidic ions. Representative examples of organic solvents include toluene, xylene, benzene, heptane, octane, decane, chlorobenzene and the like.

As mentioned above, the reaction between the halogenated silane of formula II and the reaction mixture containing the polysulfidic ion is conducted in the presence of an aqueous phase. The volume of water that is present may vary and may be the saturated NaCl aqueous solution from the first reaction. The concentration of the two reactants (compound of formula II and polysulfidic ion) in the aqueous phase generally ranges from about 20 to 50 percent by weight. Preferably, the concentration of the sulfide and sulfur in the aqueous phase ranges from about 25 to 45 percent.

For the reaction between the polysulfidic ion and the compound of formula II, additional amounts (in addition to the NaCl present in the brine for the first reaction) may be added. Examples of such salts may be of the formula

XY      VI or $X_2SO_4$      VII wherein X is selected from the group consisting of Li, Na, K, Rb and $C_s$; and wherein Y is selected from the group consisting of F, Cl and Br. Representative examples of such salts include LiF, LiCl, LiBr, $Li_2SO_4$, NaF, NaCl, NaBr, $Na_2SO_4$, KF, KCl, KBr, $K_2SO_4$, RbCl, RbBr, $Rb_2SO_4$, CsCl, CsBr and $Cs_2SO_4$. Whereas the amount of salt may vary, the salt is generally present in an amount ranging from 10 percent by weight of the aqueous solution to full or complete saturation of the aqueous solution. Obviously, an excess of salt (more than full saturation) may be used; however, no additional benefit has been found. In addition, as one can appreciate, all of the various salts mentioned above have varying levels of solubility in an aqueous solution; however, the solubility of such salts are well known. In the context of saturation of the aqueous phase, it should be calculated at the desired reaction temperature since solubility of such salts in an aqueous phase are related to the temperature of the aqueous phase. Preferably, the amount of salt that is present in the aqueous phase ranges from 20 weight percent to complete or full saturation. If supplemental salt is desired, it may be added to the reaction vessel at any time so long as it is present during the reaction.

In accordance with the preferred embodiment of the present invention, the polysulfidic ion and salt are dissolved or dispersed in the aqueous phase. A solvent such as toluene or xylene is then added, followed by the halogenated silane compound of formula II. The mixture is then heated, optionally under an inert atmosphere. The mixture may be heated to a temperature ranging from about 60° to 100° C., with a temperature of from 75° to 95° C. being preferred. The appropriate amount of phase transfer catalyst is then added to the reaction mixture as a solid or as a concentrated aqueous solution. The progress of the reaction may then be followed by G.C. or other analytical techniques. Upon filtration, the filtrate is separated into the aqueous phase and organic phase containing the desired product. Any unreacted reagents and/or solvent are removed from the organic phase by stripping at reduced pressure to yield the desired product as the pot residue.

In addition to the polysulfidic ion and halogenated silane, an additional reactant of the formula:

Alk—X      (VIII)

where X is previously defined may be present in those instances where unsymmetrical organosilicon compounds are desired in addition to those organosilicon compounds of formula I previously described.

The unsymmetrical organosilicon compounds are of the formula

Alk—$S_n$—Alk—Z      (IX)

where n, Alk and Z are as previously defined. As can be appreciated, Alk is a divalent hydrocarbon of 1 to 18 carbon atoms; and, therefore, to avoid duplication, the representative list of unsymmetrical compounds incorporate "alkyl" in their name whereas one skilled in the art appreciates it would be methyl, ethyl, propyl, butyl, etc, and up to octyldecyl, depending on the reactants used. Such representative unsymmetrical compounds include: 3-bis(trimethoxysilylpropyl) n-alkyl disulfide, 3-bis(triethoxysilylpropyl) n-alkyl tetrasulfide, 3-bis(triethoxysilylpropyl) n-alkyl octasulfide, 3-bis(trimethoxysilylpropyl) n-alkyl tetrasulfide, 2-bis(triethoxysilylethyl) n-alkyl tetrasulfide, 3-bis(trimethoxysilylpropyl) n-alkyl trisulfide, 3-bis(triethoxysilylpropyl) n-alkyl trisulfide, 3-bis(tributoxysilylpropyl) n-alkyl disulfide, 3-bis(trimethoxysilylpropyl) n-alkyl hexasulfide, 3-bis(trimethoxysilylpropyl) n-alkyl octasulfide, 3-bis(trioctoxysilylpropyl) n-alkyl tetrasulfide, 3-bis(trihexoxysilylpropyl) n-alkyl disulfide, 3-bis (triisooctoxysilylpropyl) n-alkyl tetrasulfide, 3-bis(tri-t-butoxysilylpropyl) n-alkyl disulfide, 2-bis(methoxy diethoxy silyl ethyl) n-alkyl tetrasulfide, 2-bis(tripropoxysilylethyl) n-alkyl pentasulfide, 3-bis(tricyclonexoxysilylpropyl) n-alkyl tetrasulfide, 3-bis(tricyclopentoxysilylpropyl) n-alkyl trisulfide, 2-bis(dimethyl methoxysilylethyl) n-alkyl disulfide, 2-bis(dimethyl sec.butoxysilylethyl) n-alkyl trisulfide, 3-bis(methyl butylethoxysilylpropyl) n-alkyl tetrasulfide, 3-bis(di t-butylmethoxysilylpropyl) n-alkyl tetrasulfide, 2-bis(phenyl methyl methoxysilylethyl) n-alkyl trisulfide, 3-bis(diphenyl isopropoxysilylpropyl) n-alkyl tetrasulfide, 3-bis(diphenyl cyclohexoxysilylpropyl) n-alkyl disulfide, 3-bis(dimethyl ethylmercaptosilylpropyl) n-alkyl tetrasulfide, 2-bis(methyl dimethoxysilylethyl) n-alkyl trisulfide, 2-bis(methyl ethoxypropoxysilylethyl) n-alkyl tetrasulfide, 3-bis(diethyl methoxysilylpropyl) n-alkyl tetrasulfide, 3-bis(ethyl di-sec. butoxysilylpropyl) n-alkyl disulfide, 3-bis(propyl diethoxysilylpropyl) n-alkyl disulfide, 3-bis-(butyl dimethoxysilylpropyl) n-alkyl trisulfide, 3-bis(phenyl dimethoxysilylpropyl) n-alkyl tetrasulfide, 4-bis(trimethoxysilylbutyl) n-alkyl tetrasulfide, 6-bis(triethoxysilylhexyl) n-alkyl tetrasulfide, 12-bis(triisopropoxysilyl dodecyl) n-alkyl disulfide, 18-bis(trimethoxysilyloctadecyl) n-alkyl tetrasulfide, 18-bis(tripropoxysilyloctadecenyl) n-alkyl tetrasulfide, 4-bis(trimethoxysilyl-buten-2-yl) n-alkyl tetrasulfide, 4-bis(trimethoxysilylcyclohexylene) n-alkyl tetrasulfide, 5-bis(dimethoxymethylsilylpentyl) n-alkyl trisulfide, 3-bis(trimethoxysilyl-2-methylpropyl) n-alkyl tetrasulfide and 3-bis(dimethoxyphenylsilyl-2-methylpropyl) n-alkyl disulfide.

This invention is illustrated by the following working example which is presented merely for the purpose of illustration and is not intended to be limiting the scope of the invention. Unless specifically indicated otherwise, parts and percentages are given by weight.

EXAMPLE 1

Preparation of Bis-(3-triethoxysilylpropyl) polysulfide

A 1-liter, three-neck, round-bottomed flask equipped with a mechanical paddle stirrer, reflux condenser and thermometer was charged with 12.0 g (0.30 moles) of solid sodium hydroxide pellets, 100 ml of saturated aqueous sodium chloride solution and 6.4 g (0.20 moles) of elemental sulfur. The mixture was stirred while heating to 95° C. and held at this temperature for 10 minutes. A clear red solution formed during this period. The solution was then cooled to 80° C. and a solution of 75 ml of toluene and 48.0 g (0.20 moles) of 3-chloropropyltriethoxysilane (CPTES) was added. The mixture was reheated to 80° C. with continued stirring (ca. 300–400 rpm) before adding 2.0 g (0.00031 moles) of a 50 percent aqueous solution of tetrabutylammonium bromide all at once. The color of the solution immediately turns dark upon addition of the catalyst and the temperature of the reaction mixture gradually increases to 90° to 92° C. within a few minutes before subsiding. The mixture was reacted for a total of 30 minutes after catalyst addition keeping the reaction temperature at about 80° C. During this period, the formation of some insoluble polymer was noted. Gas chromatographic analysis of the liquid organic phase indicated that the predominant components of the mixture were 57 percent starting material (CPTES), 25.4 percent bis-(3-triethoxysilylpropyl) disulfide (I) and 14.6 percent bis-(3-triethoxysilylpropyl) trisulfide (II). The isolated insoluble polymer weighed 11.9 g.

EXAMPLE 2

Preparation of Bis-(3-triethoxysilylpropyl) polysulfide

The procedure of Example 1 repeated except that an additional 25 g of solid sodium chloride was added to the initial ingredients. G.C. analysis of the organic liquid phase showed 69.3 percent starting CPTES, 21.4 percent bis-(3-triethoxysilylpropyl) disulfide and 6.3 percent bis-(3-triethoxysilylpropyl) trisulfide. The isolated insoluble polymer weighed 16.5 g.

EXAMPLE 3

Preparation of Bis-(3-triethoxysilylpropyl) polysulfide

The procedure of Example 1 was repeated except that the levels of both sulfur and sodium hydroxide were doubled. The mixture refluxed very vigorously at 82° C. G.C. analysis of the organic liquid phase showed results similar to Example 2. The isolated insoluble polymer weighed 4.0 g.

EXAMPLE 4

Preparation of Bis-(3-triethoxysilylpropyl) polysulfide

The procedure of Example 1 was repeated except that the sulfur level was doubled and the aqueous solution of the catalyst was added by addition funnel over 1 minute. G.C. analysis of liquid organic phase showed 30.4 percent starting CPTES, 38.2 percent of bis-(3-triethoxysilylpropyl) disulfide and 29.7 percent of bis-(3-triethoxysilylpropyl) trisulfide. No polymer formation was observed.

EXAMPLE 5

Preparation of Bis-(3-triethoxysilylpropyl) polysulfide

The procedure of Example 1 was repeated except that 25.6 g (0.80 moles) of sulfur and 17.0 g (0.425 moles) of sodium hydroxide were used. After 30 minutes, the G.C. analysis indicated substantial CPTES remaining. At this point, another 2.0 g addition of the 50 percent aqueous catalyst solution was added and the mixture stirred at 80° C. for another 30 minutes. G.C. analysis showed only a trace of CPTES with 26.7 percent of bis-(3-triethoxysilylpropyl) disulfide and 65.5 percent of bis-(3-triethoxysilylpropyl) trisulfide. No polymer formation was observed.

After phase separation and removal of the toluene, pale yellow needles (sulfur) crystallized from the crude product (2.4 g). The residual liquid was then stripped under high vacuum (0.15 mm Hg) to an overhead temperature of 110° C. to remove toluene and tri-n-butylamine (catalyst breakdown product) to give 45.1 g of amber liquid. Proton and C-13 NMR analysis of this material indicted the following mole fraction composition:

| | |
|---|---|
| $S_2$ | 0.141 |
| $S_3$ | 0.278 |
| $S_4$ | 0.264 |
| $S_5$ | 0.162 |
| $S_6$ | 0.105 |
| $S_7$–$S_8$ | 0.051 |
| | 1.000 |

While certain representative embodiment and details have been shown for the purpose of illustrating the invention, it will be apparent to those skilled in the art that various changes and modifications may be made therein without departing from the spirit or scope of the invention.

What is claimed is:

1. A process for the production of organosilicon compounds of the formula $$Z-\text{Alk}-S_n-\text{Alk}-Z \quad \text{(I)}$$

in which Z is selected from the group consisting of $$-\underset{\underset{R^2}{|}}{\overset{\overset{R^1}{|}}{\text{Si}}}-R^1, \quad -\underset{\underset{R^2}{|}}{\overset{\overset{R^1}{|}}{\text{Si}}}-R^2 \quad \text{and} \quad -\underset{\underset{R^2}{|}}{\overset{\overset{R^2}{|}}{\text{Si}}}-R^2$$

where $R^1$ is an alkyl group of 1 to 4 carbon atoms, cyclohexyl or phenyl;

$R^2$ is alkoxy of 1 to 8 carbon atoms, or cycloalkoxy of 5 to 8 carbon atoms;

Alk is a divalent hydrocarbon of 1 to 18 carbon atoms and n is an integer of 2 to 8; comprising (A) reacting sodium hydroxide with sulfur in the presence of a saturated NaCl aqueous solution; to form a reaction mixture; and (B) reacting said reaction mixture with a compound of the formula:

$$Z-\text{Alk-X} \quad \text{(II)}$$

where X is Cl or Br in the presence of a phase transfer catalyst.

2. The process of claim 1 wherein Z is:

$$-\underset{\underset{R^2}{|}}{\overset{\overset{R^2}{|}}{\text{Si}}}-R^2$$

$R^2$ is an alkoxy of 2 to 4 carbon atoms, n is an integer of from 2 to 4, and Alk is a divalent hydrocarbon of 2 to 4 carbon atoms.

3. The process of claim 1 wherein X is Cl.

4. The process of claim 2 wherein R is an alkoxy of 2 carbon atoms.

5. The process of claim 1 wherein the reaction between said reaction mixtures and compound of formula II is carried out at a temperature ranging from 60° C. to 100° C.

6. The process of claim 1 wherein the reaction is conducted in the presence of an aqueous phase and an organic phase.

7. The process of claim 1 wherein the phase transfer catalyst is selected from formulae:

$$\underset{\underset{R^5}{|}}{\overset{\overset{R^6}{|}}{R^4-A^+-R^7}} \quad \text{(III)}$$

$$\underset{\underset{R^9}{|}}{R^8-N^+}=C\overset{R^{10}}{\underset{R^{11}}{\diagdown}} \quad \text{(IV)}$$

$$\underset{\underset{R^{13}}{|}}{(R^{12})_2-A^+}-(CH_2)_y-\underset{\underset{R^{13}}{|}}{A^+-(R^9)_2} \quad \text{(V)}$$

wherein A represents nitrogen, phosphorus or arsenic; $R^4$, $R^5$, $R^6$, $R^7$, which my be the same or different, are each a linear or branched chain alkyl radical containing from 1 to 16 carbon atoms, optionally substituted with a phenyl, hydroxyl, halo, nitro, alkoxy or alkoxycarbonyl substituent; a linear or branched chain alkenyl radical containing from 2 to 12 carbon atoms; an aryl radical containing from 6 to 10 carbon atoms, optionally substituted by one or more alkyl substituents containing from 1 to 4 carbon atoms or alkoxy, alkoxycarbonyl or halo substituents; and with the proviso that any two of said radicals $R^4$ to $R^7$ may together form a single linear or branched chain alkylene, alkenylene or alkadienylene radical containing from 3 to 6 carbon atoms, $R^8$, $R^9$, $R^{10}$, $R^{11}$, which also may be the same or different, are each a linear or branched chain alkyl radical containing from 1 to 4 carbon atoms; with the proviso that the $R^{10}$, and $R^{11}$ radicals may together form an alkylene radical containing from 3 to 6 carbon atoms; and with the further proviso that the $R^9$ and $R^{10}$ or $R^9$ and $R^{11}$ radicals may together form an alkylene, alkenylene or alkadienylene radical containing 4 carbon atoms and, together with the nitrogen atom, comprising a 5-membered nitrogen heterocycle; $R^{12}$ is a linear or branched chain alkyl radical containing from 1 to 4 carbon atoms, or a phenyl radical; $R^{13}$ is a linear or branched chain alkyl radical containing from 1 to 4 carbon atoms, and which may be the same or different from $R^{12}$, a linear or branched chain alkenyl radical containing from 2 to 12 carbon atoms; and y is an integer greater than or equal to 1 and less than or equal to 10.

8. The process of claim 7 wherein said phase transfer catalyst is selected from the group of cations consisting of tetramethylammonium, triethylmethylammonium, tributylmethylammonium, trimethyl(n-propyl)ammonium, tetraethylammonium, tetrabutylammonium, dodecyltrimethylammonium, methyltrioctylammonium, heptyltributylammonium, tetrapropylammonium, tetrapentylammonium, tetrahexylammonium, tetraheptylammonium, tetraoctylammonium, tetradecylammonium, butyltripropylammonium, methyltributylammonium, pentyltributylammonium, methyldiethylpropylammonium, ethyldimethylpropylammonium, tetradodecylammonium, tetraoctadecylammonium, hexadecyltrimethylammonium, benzyltrimethylammonium, benzyldimethylpropylammonium, benzyldimethyloctylammonium, benzyltributylammonium, benzyltriethylammonium, phenyltrimethylammonium, benzyldimethyltetradecylammonium, benzyldimethylhexadecylammonium, dimethyldiphenylammonium, methyltrialkyl($C_8$-$C_{10}$) ammonium, methyltriphenylammonium, buten-3-yltriethylammonium, N,N-dimethyl-tetramethyleneammonium, N,N-diethyl-tetramethyleneammonium, tetramethylphosphonium, tetrabutylphosphonium, ethyltrimethylphosphonium, trimethylpentylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri(isopropyl)phosphonium, methyl-tri(n-propyl)phosphonium, methyl-tri(n-butyl)phosphonium, methyl-tri(2-methylpropyl)phosphonium, methyltricyclohexylphosphonium, methyltriphenylphosphonium, methyltribenzyl phosphonium, methyl-tri(4-methylphenyl)phosphonium, methyltrixylylphosphonium, diethylmethylphenylphosphonium, dibenzylmethylphenylphosphonium, ethyltriphenylphosphonium, tetraethylphosphonium, ethyl-tri(n-propyl)phosphonium, triethylpentylphosphonium, hexadecyltributylphosphonium, ethyltriphenylphosphonium, n-butyl-tri(n-propyl)phosphonium, butyltriphenylphosphonium, benzyltriphenylphosphonium, (β-phenylethyl)dimethylphenylphosphonium, tetraphenylphosphonium, triphenyl(4-methylphenyl)phosphonium, tetrakis(hydroxymethyl)phosphonium, tetrakis(2-hydroxyethyl)phosphonium, tetraphenylarsonium, N-methylpyridinium, N-ethylpyridinium, N-hexadecylpyridinium, N-methylpicolinium, 1,3-bis-2-yldimethylammonium) propane, 1,2-bis(trimethylammonium)ethane, 1,3-bis(trimethylammonium)propane, 1,4-bis(trimethylammonium)butane, and 1,3-bis(trimethylammonium)butane and selected from the group of anions consisting of $F^-$, $ClO_4^-$, $PF_6^-$, $BF_4^-$, tetraphenylborate anion, $PO_4^{-3}$, $H_2PO_4^-$, $CH_3SO_3^-$,

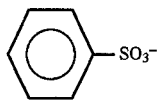

$HSO_4^-$, $NO_3^-$, $SO_4^{-2}$, $Cl^-$, and $Br^-$.

9. The process of claim 1 wherein said phase transfer catalyst is tetrabutyl ammonium bromide.

10. The process of claim 1 wherein said phase transfer catalyst is an onium salt that is present in an amount ranging from 0.1 to 10 mol percent relative to the compound of formula II.

11. The process of claim 6 wherein an organic solvent is selected from the group consisting of toluene, xylene, benzene, heptane, octane, decane, chlorobenzene and the like.

12. The process of claim 11 wherein said organic solvent is toluene.

13. The process of claim 1 wherein the reaction between the reaction mixture containing a polysulfidic ion and compound of formula II is conducted in the presence of a salt of one of the following formulae $$XY \qquad\qquad VI$$

or $$X_2SO_4 \qquad\qquad VII$$

wherein X is selected from the group consisting of Li, Na, K, Rb and Cs; and wherein Y is selected from the group consisting of Fl, Cl and Br.

14. The process of claim 13 wherein said salt is NaCl.

15. The process of claim 13 wherein said salt is present in an amount ranging from 10 weight percent of the aqueous solution to full saturation of the aqueous solution.

16. The process of claim 1 wherein, in addition to a compound (D) is present and is of the formula:

$$Alk\!-\!X \qquad\qquad (VIII).$$

17. The process of claim 1 wherein the molar ratio of the compound of formula II to the compound of formula VIII ranges from 99:1 to 1:1.

* * * * *